United States Patent
Lee et al.

(10) Patent No.: US 11,944,949 B2
(45) Date of Patent: Apr. 2, 2024

(54) SOLVENT REMOVING APPARATUS AND METHOD OF MANUFACTURING MICROSPHERE USING THE SAME

(71) Applicant: Inventage Lab Inc., Gyeonggi-do (KR)

(72) Inventors: Sanghun Lee, Seoul (KR); Chan Hee Chon, Gyeonggi-do (KR); Ju Hee Kim, Gyeonggi-do (KR)

(73) Assignee: INVENTAGE LAB INC., Gyeonggi-Do (KR)

( * ) Notice: Subject to any disclaimer, the term of this patent is extended or adjusted under 35 U.S.C. 154(b) by 0 days.

(21) Appl. No.: 18/083,670

(22) Filed: Dec. 19, 2022

(65) Prior Publication Data

US 2023/0191352 A1    Jun. 22, 2023

(30) Foreign Application Priority Data

Dec. 22, 2021 (KR) .................. 10-2021-0184474

(51) Int. Cl.
*B01J 13/12* (2006.01)
*A61K 9/16* (2006.01)
(Continued)

(52) U.S. Cl.
CPC ............. *B01J 13/12* (2013.01); *A61K 9/1694* (2013.01); *B01D 17/0214* (2013.01);
(Continued)

(58) Field of Classification Search
CPC . B01J 13/12; B01J 13/02; B01J 19/006; B01J 19/0066; A61K 9/1694;
(Continued)

(56) References Cited

U.S. PATENT DOCUMENTS 4,240,905 A * 12/1980 Scaccia ................. B01F 23/233
162/57
5,078,505 A * 1/1992 Nyman ................. B01F 27/86
366/292
(Continued)

FOREIGN PATENT DOCUMENTS

CN        102089376 A      6/2011
CN        204051611 U      12/2014
(Continued)

OTHER PUBLICATIONS

Barbosa et al, Inexpensive Apparatus for Fabricating Microspheres for 5-fluoracil Controlled Release Systems, International Journal of Chemical Engineering. (Year: 2018).*
(Continued)

*Primary Examiner* — Liam Royce
(74) *Attorney, Agent, or Firm* — The PL Law Group, PLLC

(57) ABSTRACT

A solvent removing apparatus includes a container containing an emulsion comprising a first raw material of a continuous phase and a second raw material of a dispersed phase, an impeller rotating in the container to stir the emulsion, and a foam breaker spaced apart from the impeller on an upper portion of the impeller, positioned below a surface of the emulsion to be submerged in the emulsion when the emulsion is calm, and rotating to reduce foam generated during stirring of the emulsion.

10 Claims, 10 Drawing Sheets

(51) Int. Cl.
  *B01D 17/02* (2006.01)
  *B01D 17/04* (2006.01)
  *B01D 19/02* (2006.01)
  *B01F 27/191* (2022.01)
  *B01F 27/86* (2022.01)
  *B01F 35/53* (2022.01)
  *B01J 19/00* (2006.01)

(52) U.S. Cl.
  CPC ........... *B01D 17/041* (2013.01); *B01D 19/02* (2013.01); *B01F 27/191* (2022.01); *B01F 27/86* (2022.01); *B01J 19/006* (2013.01); *B01J 19/0066* (2013.01); *B01F 35/5312* (2022.01)

(58) Field of Classification Search
  CPC .. B01D 17/041; B01D 17/0214; B01D 19/02; B01D 19/04; B01F 27/86; B01F 27/191; B01F 35/5312
  See application file for complete search history.

(56) References Cited

U.S. PATENT DOCUMENTS

| | | | | |
|---|---|---|---|---|
| 5,612,219 | A * | 3/1997 | Rodicio | C12M 41/02 422/224 |
| 5,945,126 | A * | 8/1999 | Thanoo | A61K 9/1647 424/425 |
| 2002/0089073 | A1 * | 7/2002 | Dijk | B01F 27/86 261/87 |
| 2016/0000713 | A1 | 1/2016 | Sebring | |
| 2022/0241748 | A1 * | 8/2022 | Hutchinson | B01J 19/0066 |
| 2023/0346707 | A1 * | 11/2023 | Kim | A61K 9/1694 |

FOREIGN PATENT DOCUMENTS

| | | |
|---|---|---|
| CN | 105189617 A | 12/2015 |
| EP | 1 537 846 A1 | 6/2005 |
| KR | 10-2005-0109384 A | 11/2005 |
| KR | 10-2019-0084276 A | 7/2019 |
| KR | 10-2283250 B1 | 7/2021 |
| WO | WO 92/08743 A1 | 5/1992 |
| WO | WO 2014/094793 A1 | 6/2014 |

OTHER PUBLICATIONS

Office action dated Mar. 28, 2022 from Korean Patent Office in a counterpart Korean Patent Application No. 10-2021-0184474 (all the cited references are listed in this IDS.) (English translation is also submitted herewith.).

European Search Report For EP22213457.9 dated May 23, 2023 from European patent office in a counterpart European patent application.

Database WPI Week 2021006, Thomson Scientific, London, GB; AN 2021-89762M XP002809263.

Database WPI Week 200676, Thomson Scientific, London, GB; AN 2006-737287 XP002809264.

* cited by examiner

| | Foam Breaker near surface | Foam Breaker in the depth |
|---|---|---|
| Residual solvent (ppm) | 378.0 | 154.6 |
| Encapsulation rate (%) | 94.3 | 91.7 |
| Particle size (μm) | 38.2 | 38.5 |
| C.V. (%) | 10.3 | 10.0 |
| SEM Geometry image |  Foam Breaker near surface |  Foam Breaker in the depth |

| | Primary Reference condition | Primary Reference condition repeatability |
|---|---|---|
| Residual solvent (ppm) | 169.0 | 130.1 |
| Encapsulation rate (%) | 96.3 | 97.1 |
| Particle size (μm) | 43.2 | 40.8 |
| C.V. (%) | 8.1 | 6.7 |

SOLVENT REMOVING APPARATUS AND METHOD OF MANUFACTURING MICROSPHERE USING THE SAME

CROSS-REFERENCE TO RELATED APPLICATION AND CLAIM OF PRIORITY

This application claims the benefit under 35 USC § 119 of Korean Patent Application No. 10-2021-0184474, filed on Dec. 22, 2021 in the Korea Intellectual Property Office, the entire disclosure of which is incorporated herein by reference for all purposes.

BACKGROUND

1. Field

Exemplary embodiments of the inventive concept relate to a solvent removing apparatus and method of manufacturing microsphere using the same. More particularly, exemplary embodiments of the inventive concept relate to a solvent removing apparatus for extracting and removing the solvent of an emulsion used in microsphere production, and method of manufacturing microsphere using the solvent removing apparatus.

2. Description of the Related Art

One of the drug delivery systems currently being actively researched, developed and utilized is the so-called Polymeric Drug-Delivery System ("PDDS"), which utilizes biodegradable, biocompatible and non-toxic polymers such as polylactic acid (PLA)/polyglycolic (PGA) polymers to administer a certain amount of a therapeutic agent over a long period of time, circulating doses allow controllable release of both hydrophilic and hydrophobic therapeutic agents.

These biodegradable polymers can be prepared in the form of microspheres by various known techniques. In the preparation of these biodegradable polymer microspheres, the most frequently used method is to dissolve the biodegradable polymer or the material to be encapsulated with the biodegradable polymer (drug or other active agent) in a solvent using a known method, and to disperse or emulsify in an aqueous solution containing a surfactant. And then after removing the solvent from the microspheres, and drying, a microsphere product is obtained. Since toxic solvents such as dichloromethane or chloroform are mainly used to dissolve biodegradable polymers and active agents in the microsphere manufacturing process according to the known technology, sufficient time and effort must be spent on solvent removal so that these solvents do not remain in the microsphere product, which is the final product. Accordingly, the time required to obtain the microsphere product increases and acts as an impediment to mass production. Accordingly, efforts have been made to mass-produce high-quality microspheres at low cost.

In particular, technologies related to various solvent removing apparatuses for solvent removal have been developed, but in general, by using an impeller and stirrer coupled to a rotation shaft that rotates using a motor, the solvent is extracted and removed through stirring of the emulsion, but a more effective method for this is not presented.

SUMMARY

One or more exemplary embodiment of the inventive concept provides a solvent removing apparatus.

One or more exemplary embodiments of the inventive concept also provide method of manufacturing microsphere According to an exemplary embodiment of the inventive concept, a solvent removing apparatus includes a container containing an emulsion including a first raw material of a continuous phase and a second raw material of a dispersed phase, an impeller rotating in the container to stir the emulsion, and a foam breaker spaced apart from the impeller on an upper portion of the impeller, positioned below a surface of the emulsion to be submerged in the emulsion when the emulsion is calm, and rotating to reduce foam generated during stirring of the emulsion.

In an exemplary embodiment, the solvent removing apparatus may include a rotation shaft connected to the impeller to provide rotational force to the impeller. The foam breaker may be connected to the rotation shaft, and the impeller and the foam breaker rotate simultaneously by the rotation of the rotation shaft.

In an exemplary embodiment, when a depth from the surface of the emulsion to a center of the foam breaker is defined as $H_{fb}$, and a depth from the surface to a bottom surface of the container is defined as $H_{liquid}$, $H_{fb}/H_{liquid}$ may satisfy 0.2 to 0.5.

In an exemplary embodiment, when a diameter of the impeller is defined as $D_{main}$ and a diameter of the foam breaker is defined as $D_{fb}$, $D_{fb}/D_{main}$ may satisfy 0.3 to 1.

In an exemplary embodiment, when an inside of the container has a cylindrical shape, a diameter of the container is defined as $D_{tank}$, and a diameter of the foam breaker is defined as $D_{fb}$, $D_{fb}/D_{tank}$ may satisfy 0.3 to 0.6.

In an exemplary embodiment, the solvent removing apparatus may include a compressed air supply unit for supplying compressed air to the surface of the emulsion in the container and an air discharge unit for discharging air in the container to an outside of the container.

In an exemplary embodiment, when a depth from the surface of the emulsion to a center of the foam breaker is defined as $H_{fb}$ and a diameter of the foam breaker is defined as $D_{fb}$, the value of $H_{fb}/D_{fb}$ may be between 0.5 and 2.

In an exemplary embodiment, the container may include at least one baffle formed on an inner wall of the container, protruding toward a center of the container.

In an exemplary embodiment, when a height from a bottom of the baffle to the surface of the emulsion is defined as $H_{baffle}$ and a height from a bottom of the container to the surface of the emulsion is defined as $H_{liquid}$, $H_{baffle}/H_{liquid}$ may satisfy 0.6 to 0.8.

In an exemplary embodiment, when an inside of the container has a cylindrical shape, a height of the baffle protruding from the inner wall of the container is defined as $W_{baffle}$, and a diameter of the container is defined as $D_{tank}$, $W_{baffle}/D_{tank}$ may satisfy 0.06 to 0.10.

In an exemplary embodiment, the solvent removing apparatus may include a compressed air supply unit for providing compressed air to a space above the emulsion in the container, and an air discharge pump for discharging air in the space to an outside of the container.

According to the exemplary embodiments of the present inventive concept, a method of manufacturing microsphere includes preparing a first raw material and preparing a second raw material including a biodegradable polymer, drug and solvent, forming an emulsion including the first raw material in a continuous phase and the second raw material in a dispersed phase using the first raw material and the second raw material, providing the emulsion to a solvent removing apparatus, and solvent extraction removal step of extracting and removing the solvent of the dispersed phase of the emulsion by rotating an impeller and a foam breaker of the solvent removing apparatus. The solvent removing apparatus includes a container for accommodating the emulsion, the impeller rotating in the container to stir the emulsion, and the foam breaker spaced apart from the upper portion of the impeller, positioned below a surface of the emulsion to be submerged in the emulsion when the emulsion is calm, and rotating to reduce foam generated during stirring of the emulsion.

In an exemplary embodiment, in the solvent extraction removal step, when a depth from the surface of the emulsion to a center of the foam breaker is defined as $H_{fb}$, and a depth from the surface to a bottom surface of the container is defined as $H_{liquid}$, $H_{fb}/H_{liquid}$ may satisfy 0.5 to 0.2.

In an exemplary embodiment, in the solvent extraction removal step, when a depth from the surface of the emulsion to a center of the foam breaker is defined as $H_{fb}$, and a diameter of the foam breaker is defined as $D_{fb}$, the value of $H_{fb}/D_{fb}$ may be between 0.5 to 2.

In an exemplary embodiment, in the solvent extraction removal step, the container may include at least one baffle formed on an inner wall of the container protruding toward a center of the container.

It is to be understood that both the foregoing general description and the following detailed description are exemplary and explanatory and are intended to provide further explanation of the invention as claimed.

BRIEF DESCRIPTION OF THE DRAWINGS

The above and other features of the inventive concept will become more apparent by describing in detail exemplary embodiments thereof with reference to the accompanying drawings, in which.

DETAILED DESCRIPTION

Figure 1:
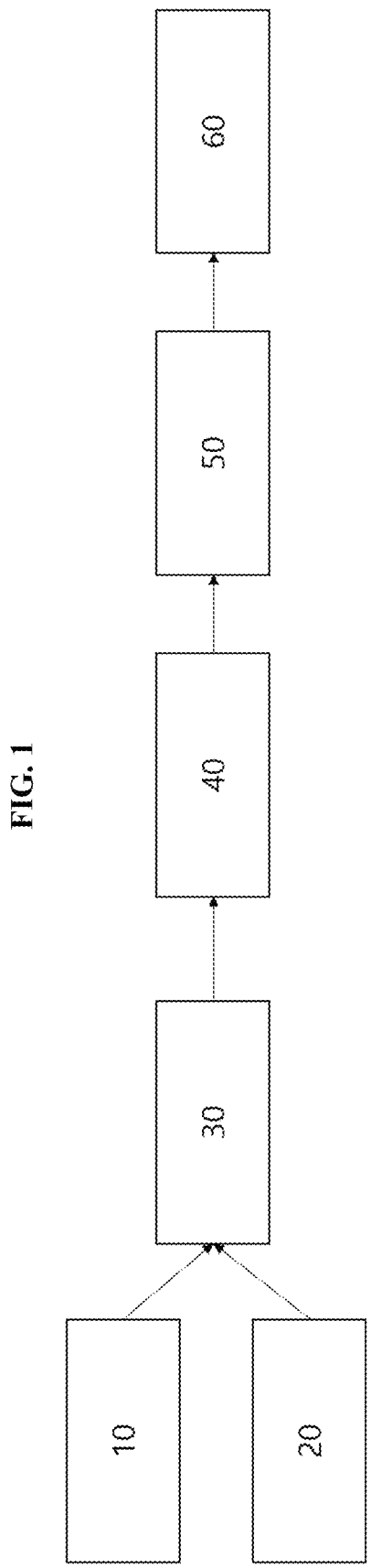
FIG. 1 is diagram illustrating a microsphere manufacturing system including a solvent removal apparatus according to an embodiment of the present invention.

Hereinafter, the inventive concept will be explained in detail with reference to the accompanying drawings.

Since the present invention may have various changes and have various forms, specific exemplary embodiments are illustrated in the drawings and described in detail in the text. However, it is not intended to limit the present invention to the specific disclosed form, and it will be appreciated that the present invention includes all modifications, equivalences, or substitutions included in the spirit and the technical scope of the present invention.

FIG. 1 is diagram illustrating a microsphere manufacturing system including a solvent removal apparatus according to an embodiment of the present invention.

Referring to FIG. 1, the microsphere manufacturing system includes a raw material storage unit, an emulsion forming unit 30, a solvent extraction removing unit 40, a washing unit 50 and a drying unit 60. The raw material storage unit may include a first raw material storage unit 10 and a second raw material storage unit 20.

The first raw material storage unit 10 may store a first raw material. The first raw material may include purified water and a surfactant. For example, the first raw material may be an aqueous solution in which polyvinyl alcohol ("PVA") is dissolved as a surfactant in pure water.

The type of the surfactant is not particularly limited, and any biodegradable polymer solution may be used as long as it can help the formation of a dispersed phase of stable droplets in an aqueous solution phase, which is a continuous phase. The surfactant may be selected preferably from methylcellulose, polyvinylpyrrolidone, carboxymethylcellulose, lecithin, gelatin, polyvinyl alcohol, polyoxyethylene sorbitan fatty acid ester and polyoxyethylene castor oil derivative and mixtures of these.

The second raw material storage unit 20 may store a second raw material. The second raw material may be an oil-phase solution, and may include an organic solvent, a biodegradable polymer dissolved therein, and a drug. The organic solvent is a solvent used to dissolve the biodegradable polymer and may not be mixed with water. The kind of organic solvent dissolving the biodegradable polymer is not particularly limited, but preferably may be selected at least one from the group consisting of dichloromethane, chloroform, ethyl acetate, acetone, acetonitrile, dimethyl sulfoxide, dimethylformamide, methyl ethyl ketone, acetic acid, methyl alcohol, ethyl alcohol, propyl alcohol, benzyl alcohol or a mixture thereof.

The type of the biodegradable polymer is not particularly limited, but polyester is preferably used, and in particular may be selected from polylactide, polyglycolide, poly(lactide-co-glycolide), poly(lactide-co-glycolide)glucose, polycaprolactone, and mixtures thereof.

The type of the drug is not particularly limited, and for example, may be selected from a dementia treatment; Parkinson's disease treatment; anticancer drugs; antipsychotic drugs, such as antianxiety drugs, antidepressants, tranquilizers, and psychotropic drugs; Cardiovascular therapeutics such as hyperlipidemia, hypertension, hypotension, antithrombotic, vasodilator, and arrhythmia; epilepsy treatment;

Gastrointestinal treatment agents such as anti-ulcer agents and the like; rheumatoid treatment; antispasmodics; tuberculosis treatment; muscle relaxants; osteoporosis treatment; erectile dysfunction treatment; styptic; hormonal agents such as sex hormones; diabetes treatment; Antibiotic; anti-fungal agents; antiviral agents; antipyretic analgesic and anti-inflammatory; autonomic modulators; corticosteroids; diuretic; antidiuretics; painkiller; anesthetic; antihistamines; antiprotozoal; anti-anemia; anti-asthma; anticonvulsants; antidote; antimigraine; antiemetic; anti-Parkinson's drugs; antiepileptic drugs; antiplatelet agents; antitussive expectorant; bronchodilator; cardiac; immunomodulators; protein drugs; gene drugs; and mixtures thereof.

Although not particularly limited among the above-mentioned drugs preferably it may be selected from the group consisting of donepezil, memantine, rivastigmine, entecavir, lamivudine, rotigotine, ropinirole, bupivacaine, ropivacaine, meroxicam, buprenorphine, fentanyl, nimodipine, granisetron, triamcinolone, Cytarabine, carmustine, tamsoleucine, folmacoxib, testosterone, estradiol, risperidone, paliperidone, olanzapine, aripiprazole, goserelin, leuprolide, tryptorelin, buserellin, naparelin, deslorrelin, jade Threotide, fasireotide, lanreotide, vapretide, exenatide, liraglutide, lixisenataide, semaglutide and salts thereof and mixtures thereof.

The emulsion forming unit 30 may receive the first raw material and the second raw material from the first raw material storage unit 10 and the second raw material storage 20, may be continuously formed an emulsion including the first raw material in a continuous phase and the second raw material in a dispersed phase by using the first raw material and the second raw material. The emulsion forming unit 30 may include a microsphere manufacturing apparatus. The microsphere manufacturing apparatus may be a microchip that forms the emulsion using micro fluidics. (Specific principles of microspheres formation using microchips will be described later in FIG. 10)

The solvent extraction removing unit 40 may receive and receive the emulsion formed from the emulsion forming unit 30 and may extract and remove the solvent form the dispersed phase of the emulsion to form microspheres containing the drug. The solvent extraction removing unit 40 may include a tank for accommodating the emulsion, a stirrer for stirring the emulsion, and a heater for heating the emulsion.

Specifically, in the solvent extraction removing unit 40, when the emulsion is maintained or stirred at a temperature below the boiling point of the organic solvent for a certain time, for example 2 hours to 48 hours, the organic solvent can be extracted as a continuous phase from a biodegradable polymer solution in the form of droplets, which is a dispersed phase. A portion of the organic solvent extracted in the continuous phase may be evaporated from the surface. As the organic solvent is extracted and evaporated from the biodegradable polymer solution in the form of droplets, the dispersed phase in the form of droplets may be solidified to form microspheres. At this time, the emulsion may be flowed or heated to accelerate extraction and evaporation. For example, by forming a fluid flow in the emulsion, the solvent of the second raw material may be extracted, and the extracted solvent may be removed by evaporation. By heating the emulsion above the boiling point of the solvent, it may be removed by vaporizing the solvent. By removing a portion of the continuous phase containing the organic solvent extracted from the dispersed phase and supplying a new aqueous solution capable of replacing the removed continuous phase, the organic solvent present in the dispersed phase may be sufficiently extracted and evaporated into the continuous phase. At this time, the new aqueous solution may optionally further include a surfactant.

The washing unit 50 may recover and wash the microspheres from the solvent extraction removing unit 40. A method of recovering and washing the microspheres from the continuous phase containing the microspheres formed from the solvent extraction removing unit 40 in not particularly limited, and after recovery using a method such as filtration or centrifugation, washing with water may be performed. Through this, the remaining organic solvent and surfactant (e.g., polyvinyl alcohol) can be removed. The washing step may be typically performed using water, and the washing step may be repeated several times.

The drying unit 60 may dry the washed microspheres to obtain a microsphere powder. After the filtration and washing steps, the obtained microspheres may be dried using a conventional drying method to finally obtain a dried microsphere powder. The method of drying the microspheres is not limited. However, the drying method used is not particularly limited, and freeze drying, vacuum drying or reduced pressure drying may be used.

Through the drying process of the microspheres, the final target monodisperse biodegradable polymer-based microsphere powder is prepared, and then, the obtained microsphere powder may be suspended in a suspension and filled into an appropriate container, such as a disposable syringe, to obtain the final product.

Figure 2:
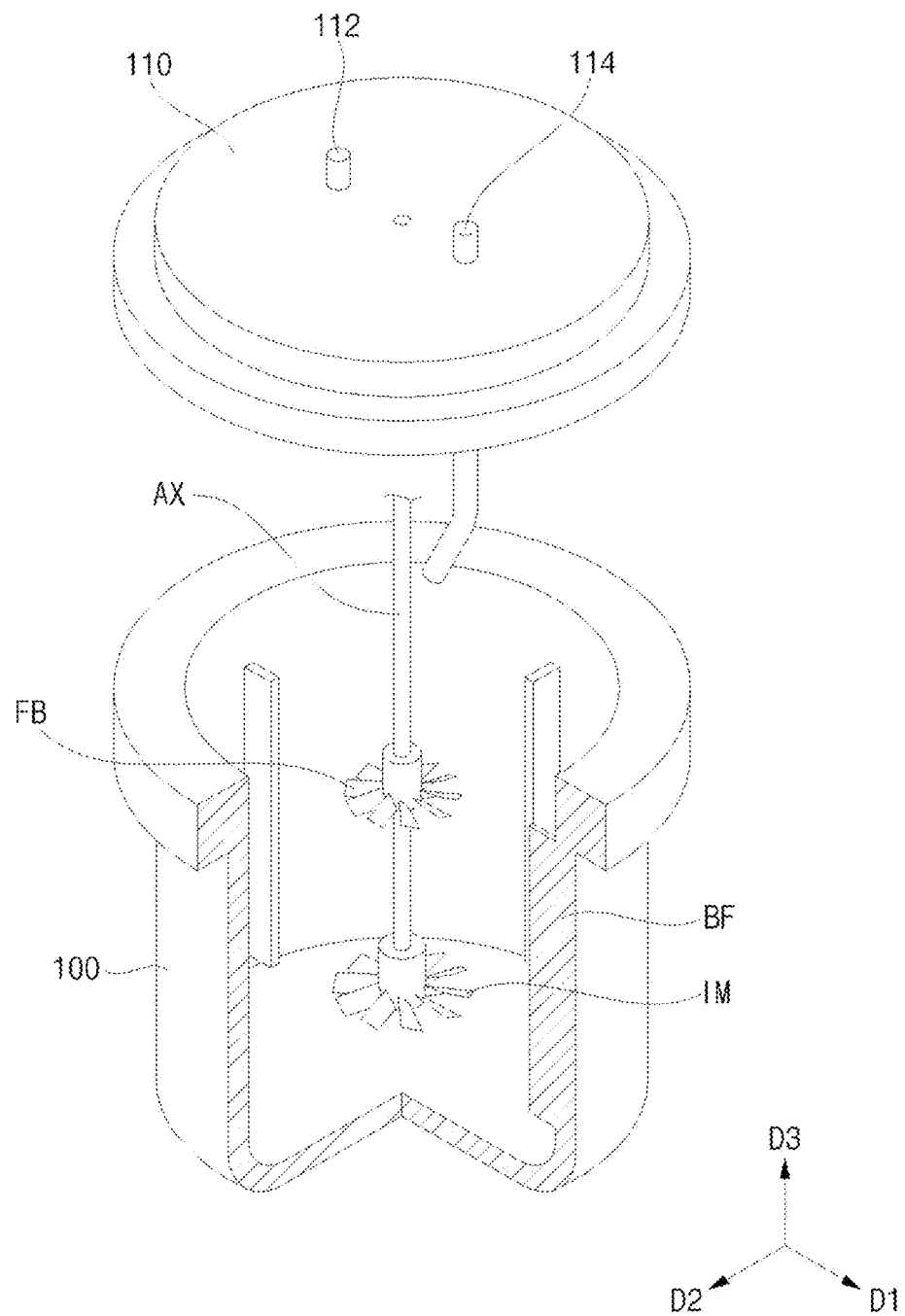
FIG. 2 is an exploded perspective view illustrating a solvent removal apparatus according to an embodiment of the present invention.
Figure 3:
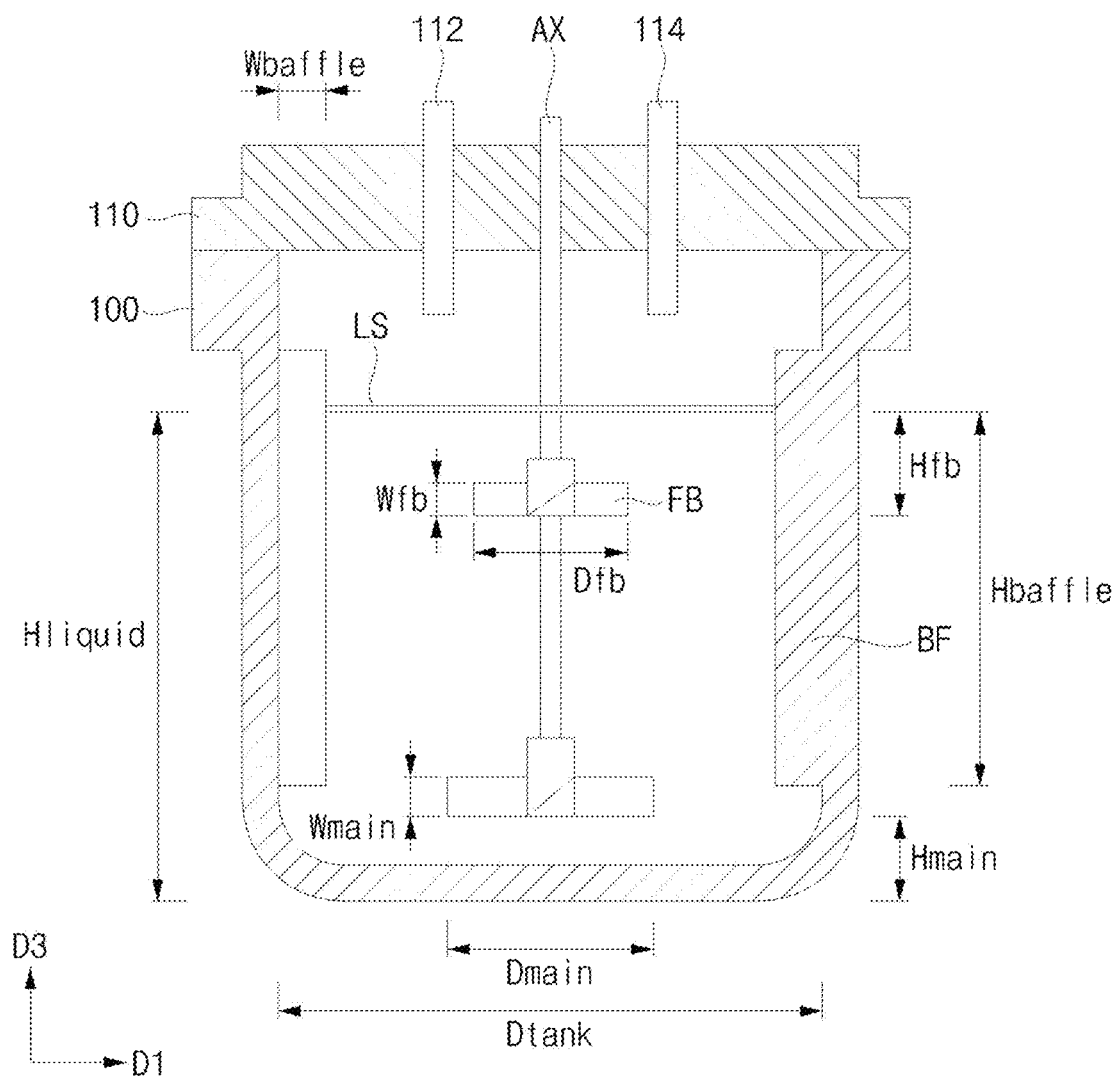
FIG. 3 is a cross-sectional view illustrating a solvent removal apparatus according to an embodiment of the present invention.

FIG. 2 is an exploded perspective view illustrating a solvent removal apparatus according to an embodiment of the present invention. FIG. 3 is a cross-sectional view illustrating a solvent removal apparatus according to an embodiment of the present invention.

Referring to FIG. 2 to FIG. 3, the solvent removal apparatus may include a container 100, a cover 110, an air discharge unit 112, a compressed air supply unit 114, an impeller IM, a foam breaker FB, a rotation shaft AX and a baffle BF.

The container 100 accommodates an emulsion including a first raw material in a continuous phase and a second raw material in a dispersed phase. The container 100 includes a bottom surface and a wall surface forming a space for accommodating the emulsion therein. The container 100 may have a cylindrical shape, but is not limited thereto.

The cover 110 is coupled to the upper portion of the container 100 to maintain airtightness of the container 100, and the air discharge unit 112 and the compressed air supply unit 114 to communicate with an inside of the container 100 may be included. In addition, a drive unit (not shown) may be positioned in the cover 110 to generate rotational force on the rotation shaft AX for rotating the impeller IM and the foam breaker FB.

The air discharge unit 112 may serve to inhale gas inside the container 100 and depressurize the inside of the container 100. Through this, the boiling point of the organic solvent is lowered, so that the organic solvent extracted in the continuous phase can be vaporized even at a low temperature. In addition, the organic solvent gas extracted an evaporated from the dispersed phase of the emulsion EM may be discharged to an outside of the container 100 through the air discharge unit 112. Through this, since the partial pressure of the organic solvent in the container 100 is lowered, continuous solvent extraction and evaporation may be performed.

The compressed air supply unit 114 may supply compressed air to the surface of the emulsion in the container 100. On the surface of the emulsion, evaporation of the solvent occurs by diffusion and convection of the solvent in the emulsion into the air. At this time, when compressed air is provided to the surface of the emulsion, by the air flow by the compressed air, the relative velocity difference between the emulsion and air rises, and accordingly, evaporation by diffusion and convection of solvent may be accelerated.

The impeller IM may be disposed in the container 100 and rotate in the container 100 to stir the emulsion. By the rotation of the impeller IM, a rotational flow is formed in the emulsion, and thus the release of the solvent in the emulsion may be accelerated. The impeller IM may have a propeller shape having a plurality of blades, but is not limited thereto.

The foam breaker FB may be located above the impeller IM and spaced apart from the impeller IM. The foam breaker FB may rotate to reduce foam generated during stirring of the emulsion. Accordingly, by improving the stirring efficiency of the emulsion and improving rotational flow as well as vertical flow in the emulsion, the evaporation of the solvent in the emulsion may be accelerated as a whole. The foam breaker FB may have a propeller shape having a plurality of blades, but is not limited thereto.

The rotation shaft AX may be located at a central axis inside the container 100 through the cover 110. The foam breaker FB and the impeller IM are connected to the rotation shaft AX, so that the impeller IM and the foam breaker FB may rotate simultaneously by the rotation of the rotation shaft AX.

The baffle BF may be structure protruding from an inner wall of the container 100 toward the center of the container 100. One or more baffle BF may be formed in the container 100 and may extend along a third direction D3 perpendicular to the first and second directions D1 and D2. In this embodiment, a case in which four baffles are formed along the circumferential direction of the inner wall of the container 100 is exemplified, but is not limited thereto.

When the emulsion in the container 100 is rotated and flowed by the rotation of the impeller IM under the influence of the baffle BF, stirring proceeds smoothly in the vertical and horizontal directions, and even when the impeller IM rotates at the same rotational speed, it can play a role in generating more bubbles (excellent stirring force).

According to this embodiment, the foam breaker FB is disposed on the impeller IM and rotates to crush bubbles generated on the surface of the emulsion during solvent removal, through this, a phenomenon in which evaporation of the solvent is blocked by bubbles at the interface between the emulsion and air can be effectively prevented.

In addition, through the rotation of the foam breaker FB, the fluidity of the emulsion in the up-and-down direction (third direction D3) is improved, with the effect of increasing the solution circulation (Surface Renewal), and the crushed small bubbles are delivered to the inside of the emulsion, and through this, an aeration effect occurs in the emulsion, and extraction and evaporation of the solvent may be accelerated.

In addition, through the application of the baffle BF, Turbulent Flow is generated in the flow of the emulsion to improve stirring, so that the concentration of the solvent may be kept uniform throughout the entire volume of the emulsion.

In addition, by the influence of the compressed air provided by the compressed air supply unit 114, solution circulation (Surface Renewal) at the interface between the emulsion and air may be increased, thereby it may accelerate the diffusion of the solvent in the emulsion into the air. In addition, under the influence of the compressed air, Turbulent Flow may be generated in the gas in the container 100, and it is possible to keep the thickness of the Diffusive Sublayer $\delta\_a$ in the air thin by rapidly lowering the solvent concentration of the gas on the surface of the emulsion, and accordingly, the solvent evaporation effect may be improved.

In addition, the air discharge unit 112 may remove air having a high solvent concentration in the container 100 from the container 100, thereby improving solvent evaporation efficiency.

Figure 4:
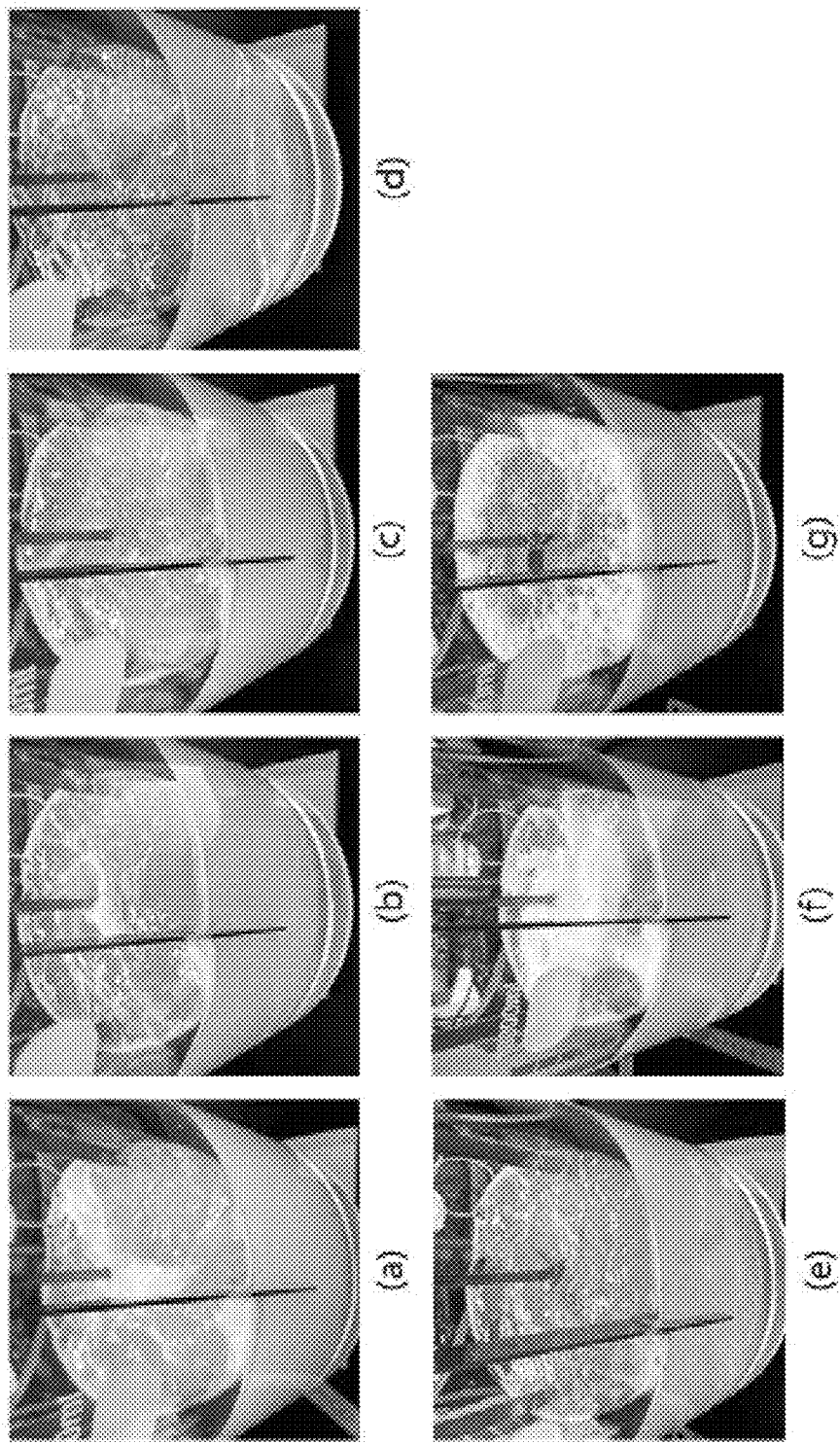
FIG. 4 is a diagram illustrating an experimental example comparing the stirring effect according to the position of the foam breaker.

FIG. 4 is a diagram illustrating an experimental example comparing the stirring effect according to the position of the foam breaker.

Referring FIG. 3 to FIG. 4, the location where foam breaker FB was installed was changed, and accordingly the amount of foam generated and reduced was compared. When the emulsion is calm, and the depth from the surface LS of the emulsion in the container 100 to the center of the foam breaker FB is defined as $H_{fb}$, and the depth from the surface LS to the bottom surface of the container is defined as $H_{liquid}$, it was confirmed that the effect of the foam breaker FB differed according to the value of $H_{fb}/H_{liquid}$.

In the experiment, the solution (emulsion) is to accommodate 4 L of ultrapure water containing 0.25% by weight of PVA in a container 100 with a volume of 10 L, and the foam breaker FB is placed on top of the impeller IM and configured to rotate by the rotation shaft AX. The rotational speed of the rotation shaft AX was 250 RMP, and after application for 15 minutes, the state of bubbles on the surface was observed.

(a) is when the value of $H_{fb}/H_{liquid}$ is 0.54, (b) is when the value of $H_{fb}/H_{liquid}$ is 0.46, (c) is when the value of $H_{fb}/H_{liquid}$ is 0.38, (d) is when the value of $H_{fb}/H_{liquid}$ is 0.31, (e) is when the value of $H_{fb}/H_{liquid}$ is 0.23, (f) is when the value of $H_{fb}/H_{liquid}$ is 0.15, (g) is when the value of $H_{fb}/H_{liquid}$ is 0.08, it is a photograph of an experimental example comparing the amount of bubbles on the emulsion surface.

In the experiment, the closer the $H_{fb}/H_{liquid}$ value is to 0, this is a case where the foam breaker FB is close to the surface of the solution (emulsion). At $H_{fb}/H_{liquid}$ value of 0.54, it may be seen that a large amount of bubbles are generated on the surface. At $H_{fb}/H_{liquid}$ value of 0.46, a small amount of bubbles stagnate on the surface of the solution, but a vortex is formed regularly on the surface of the solution, which may crush large burbles on the surface, and it may be confirmed that the foam breaker works effectively by transferring small bubbles into the solution. It was confirmed that the foam breaker worked effectively when the $H_{fb}/H_{liquid}$ value was from 0.38 to 0.23, and when the $H_{fb}/H_{liquid}$ value was 0.15 or 0.08, a large amount of bubbles were generated on the surface and the foam breaker did not work effectively.

Through this, when the value of $H_{fb}/H_{liquid}$ satisfies 0.2 to 0.5, it was confirmed that effective solvent evaporation was possible by crushing large bubbles on the surface and transferring small bubbles to the inside of the solution.

Figure 5:
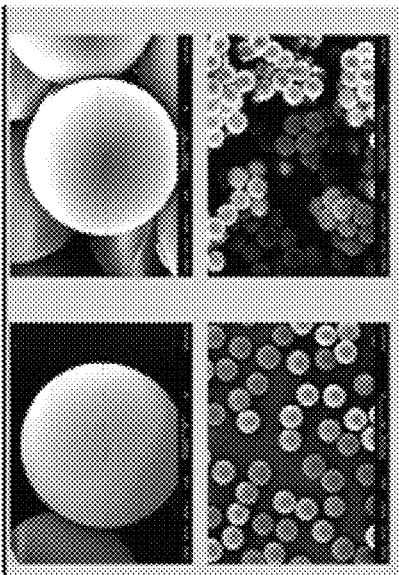
FIG. 5 is a diagram illustrating micrographs of residual solvent, encapsulation rate, particle size and shape depending on whether compressed air is applied in the solvent removal apparatus according to an embodiment of the present invention.

FIG. 5 is a diagram illustrating micrographs of residual solvent, encapsulation rate, particle size and shape depending on whether compressed air is applied in the solvent removal apparatus according to an embodiment of the present invention.

Referring to FIG. 5, when a first raw material, the aqueous phase, includes PVA 0.25% by weight and ultrapure water, and a second raw material, the oil phase, includes PLGA7504 Polymer (11.8% by weight), Finasteride (5.9% by weight), and DCM (82.3% by weight), depending on whether or not compressed air was applied, micrographs of residual solvent, encapsulation rate, particle size (size of the microspheres produced) and shape were confirmed.

In the case of applying compressed air using the compressed air supply unit 114, compared to other cases, the encapsulation rate was greatly improved, and it was confirmed that there was no significant change in residual solvent, particle size, and C.V. %.

It is confirmed that this is because the foam caused by the surfactant (PVA Surfactant) generated by stirring prevents the liquid-air interface from being covered by supplying compressed air.

On the interface between the solution and the air, the remaining solvent vapor (DCM solvent gas), which is heavier than air, is effectively pushed off the surface and moved upward, thereby reducing the concentration of the solvent near the surface of the solution. Through this, the diffusion layer (Diffusive Boundary Layer δ_a) becomes thin, so that the solvent is smoothly evaporated.

In addition, by inducing turbulent Flow of air on an upper portion of the interface between the solution and air, convention is activated, which increases the mass transfer of the solvent, and the speed difference between liquid and the fluid (Liquid, Air) is increased, the mass transfer coefficient value of the solvent in the solution inside the container is also increased, so that smooth evaporation of the solvent is achieved.

Figure 6:
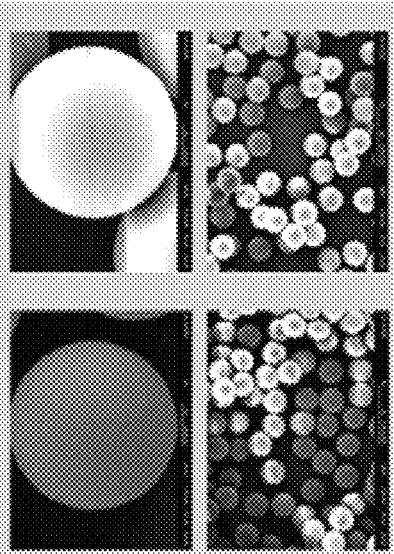
FIG. 6 is a diagram illustrating micrographs of residual solvent, encapsulation rate, particle size and shape according to whether or not the electric pump is applied in the solvent removal apparatus according to an embodiment of the present invention.

FIG. 6 is a diagram illustrating micrographs of residual solvent, encapsulation rate, particle size and shape according to whether or not the electric pump is applied in the solvent removal apparatus according to an embodiment of the present invention.

Referring FIG. 6, when the air is discharged using the air discharge unit 112, compared to the other cases, there was no significant difference in the encapsulation rate, but it was confirmed that the residual solvent was significantly reduced, and the particle size and C.V. % did not change significantly.

Figure 7:
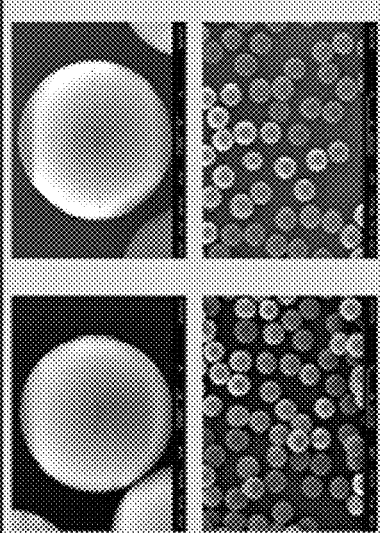
FIG. 7 is a diagram illustrating micrographs of residual solvent, encapsulation rate, particle size and shape according to the position of the foam breaker in the solvent removal apparatus according to an embodiment of the present invention.
Figure 7:
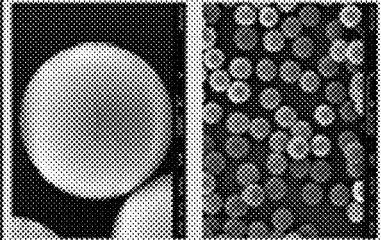

FIG. 7 is a diagram illustrating micrographs of residual solvent, encapsulation rate, particle size and shape according to the position of the foam breaker in the solvent removal apparatus according to an embodiment of the present invention.

Referring FIG. 7, there was a slight difference in the encapsulation rate and residual solvent between the case where the foam FB was applied to the surface of the solution and the case where it was applied to a depth of the solution, it is reviewed that the difference occurred somewhat because the foam breaker did not sufficiently perform the role of crushing and delivering the foam.

A propeller blade-shaped structure with a diameter of 7 cm was used as the foam breaker FB used in the experiment, and a propeller blade-shaped structure with a diameter of 11 cm was used as the impeller IM. In addition, when the foam breaker FB is applied near the surface of the solution, a depth $H_{fb}$ from the surface of the solution is $D_{fb}/2$ based on a diameter $D_{fb}$ of the foam breaker, and when the foam breaker is applied to a depth of the solution, the experiment was conducted by applying $H_{fb}$ to 1.5 $D_{fb}$.

Figure 8C:
FIGS. 8A to 8C are diagrams for comparing flowability according to whether or not baffle is applied in the solvent removal apparatus according to an embodiment of the present invention.
Figure 8B:
Figure 8A:
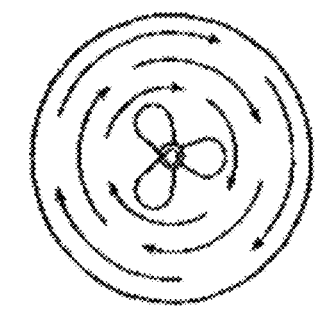
Figure 8A:
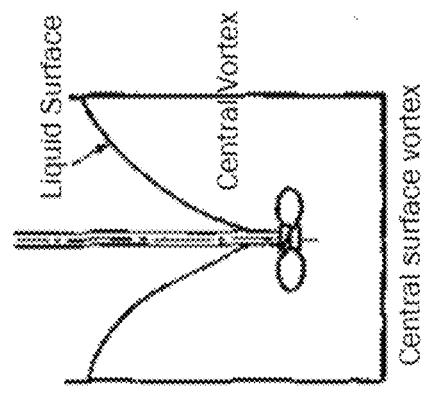

FIGS. 8A to 8C are diagrams for comparing flowability according to whether or not baffle is applied in the solvent removal apparatus according to an embodiment of the present invention.

FIG. 8A is a diagram illustrating the concept of a Vortex formed in a solution and Solid body rotation when only an impeller in a container is applied. In FIG. 8B, when the baffle BF is not applied, it is confirmed that the flow of the solution is not active in the vertical direction due to the formed vortex and solid body rotation when the rotational flow of the solution is generated. FIG. 8C confirms that when the baffle BF is applied, the formation of vortex is reduced at the same rotational speed, and the flow of the solution is active in the vertical direction.

When Solid Body Rotation occurs, solvents in a dispersed phase of the solution (emulsion) are extracted into a continuous phase, resulting in a local high concentration of the solvent, which may reduce the extraction of the solvent and at a same time may affect the solidified microspheres or may occur precipitation of the drug in the microspheres.

On the other hand, the generation of the Vortex may have an advantage of increasing the evaporation of the solvent by generating an effect of increasing the area of the Liquid-Air Interface. However, due to the Vortex, the time the solution stays on the surface near the interface becomes longer, and the vertical flow of the solution deteriorates, resulting in inhibition of solvent evaporation. In particular, the Diffusion Coefficient of the solvent inside the solution is 1.2×10^(−5) cm^2/s, which is about 10,000 times lower than Diffusion (In Air Diffusion Coefficient 0.101 cm^2/s), so that it may be seen that the inhibition of circulation in the solution is more disadvantageous for solvent evaporation than the effect of increasing the interface. In particular, for mass production of microspheres, when the size of the container is increased (Scale up), these problems may have a greater impact.

When the baffle BF is applied, the flow of the solution inside the container circulates smoothly up and down without direction, so the surface area of the Liquid-Air Interface is smaller than when a vortex is formed, but the solution is quickly replaced near the interface, as a result, it was confirmed that it is advantageous in solvent evaporation.

Figure 9:
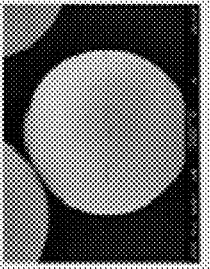
FIG. 9 is a repeated test result for an experimental example of the solvent removal apparatus according to an embodiment of the present invention.

FIG. 9 is a repeated test result for an experimental example of the solvent removal apparatus according to an embodiment of the present invention.

Referring FIG. 9, after accommodating 0.8 L of PVA in the container, applying the baffle structure, foam breaker and impeller, repeated experiments showed that even if the external conditions slightly changed, it was confirmed that the residual solvent, encapsulation rate, and particle size C.V. % could be repeated at desired levels without significant fluctuations.

Through various experiments, when the emulsion is calm, the inventors defined a depth from the surface of the emulsion to a center of the foam breaker as $H_{fb}$, and when a depth from the surface to a bottom of the container was defined as $H_{liquid}$, it was confirmed that the solvent evaporation effect was excellent when $H_{fb}/H_{liquid}$ satisfies 0.2 to 0.5.

When a diameter of the impeller is defined as $D_{main}$ and a diameter of the foam breaker is defined as $D_{fb}$, and when $D_{fb}/D_{main}$ satisfies 0.3 to 1, it was confirmed that the solvent evaporation effect was excellent.

When a diameter of the container is defined as $D_{tank}$ and a diameter of the foam breaker is defined as $D_{fb}$, it was confirmed that the solvent evaporation effect was excellent when $D_{fb}/D_{tank}$ satisfies 0.3 to 0.6.

When the emulsion is calm, and a depth from the surface of the emulsion to a center of the foam breaker is defined as $H_{fb}$ and a diameter of the foam breaker is defined as $D_{fb}$, it was confirmed that the solvent evaporation effect was excellent when the value of $H_{fb}/D_{fb}$ satisfies 0.5 to 2.

When the emulsion is calm, and a height from the bottom of the baffle to the surface of the emulsion is defined as $H_{baffle}$, and a height from the bottom of the container to the surface of the emulsion is defined as $H_{liquid}$, it was confirmed that the solvent evaporation effect was excellent when $H_{baffle}/H_{liquid}$ satisfies 0.6 to 0.8.

When a diameter of the foam breaker is defined as $D_{fb}$ and a height of the foam breaker is defined as $W_{fb}$, it was confirmed that the solvent evaporation effect was excellent when $D_{fb}/W_{fb}$ satisfies 5 to 9.

When a height of the baffle protrudes from an inner wall of the container is defined as $W_{baffle}$ and a diameter of the container is defined as $D_{tank}$, it was confirmed that the solvent evaporation effect was excellent when $W_{baffle}/D_{tank}$ satisfies 0.06 to 0.10.

Figure 10:
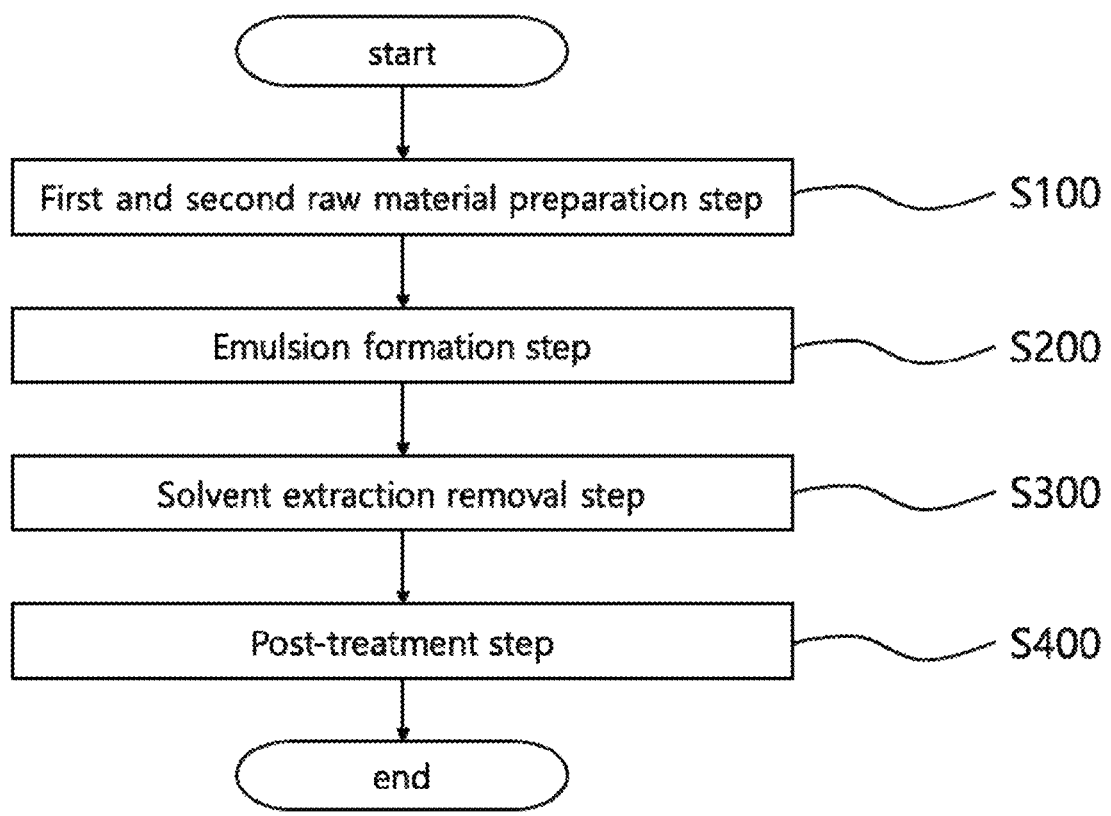
FIG. 10 is a flowchart illustrating a method for manufacturing microspheres according to an embodiment of the present invention.

FIG. 10 is a flowchart illustrating a method for manufacturing microspheres according to an embodiment of the present invention.

Referring FIG. 10, method of manufacturing microsphere may include first and second raw material preparation step S100, emulsion formation step S200, solvent extraction removal step S300 and post-treatment step S400.

In the first and second raw material preparation step S100, a first raw material may be prepared, and a second raw material including a biodegradable polymer, a drug, and a solvent may be prepared.

In this case, the first material may include Purified Water and a surfactant. The second raw material is an oil-phase solution, and may include an organic solvent, a biodegradable polymer dissolved therein, and a drug.

In the emulsion formation step S200, an emulsion including the first raw material of the continuous phase and the second raw material of the dispersed phase may be formed using the first raw material and the second raw material. For example, a method of mixing and stirring the first raw material and the second raw material, a microfluidic method of forming microsphere droplets through the flow of a microchannel, and the like may be used. The emulsion includes the first raw material in the continuous phase and the second raw material in the dispersed phase. In the solvent extraction removal step S300, the solvent of the dispersed phase of the emulsion may be removed by extraction and evaporation. For example, the impeller is located above, and spaced apart from a container for accommodating the emulsion including the first raw material of the continuous phase and the second raw material of the dispersed phase, an impeller rotating in the container to stir the emulsion, and the impeller, when the emulsion is stirred by rotation, using a solvent removing apparatus including a foam breaker to reduce generated foam, it is possible to accelerate the extraction of the solvent from the dispersed phase of the emulsion to the continuous phase and evaporation of the extracted solvent. Through this, it is possible to form solidified microspheres.

In the post-treatment step S400, the solidified microspheres are washed and dried to finally prepare the desired monodisperse biodegradable polymer-based microsphere powder, thereafter, the obtained microsphere powder may be suspended in a suspension and filled in an appropriate container, such as a disposable syringe, to perform a post-treatment process to obtain a final product.

Although the present invention has been described with reference to the above exemplary embodiments, it will be understood by those skilled in the art that various modifications and changes may be made to the present invention without departing from the spirit and scope of the present invention as set forth in the claims below.

What is claimed is:

1. An apparatus with an emulsion contained therein for removing solvent, the apparatus comprising:
   a container;
   the emulsion contained in the container, the emulsion comprising a first raw material of a continuous phase and a second raw material of a dispersed phase;
   an impeller configured to rotate in the container to stir the emulsion; and
   a foam breaker spaced apart from the impeller on an upper portion of the impeller, the foam breaker positioned below a surface of the emulsion to be submerged in the emulsion, the foam breaker configured for rotating to reduce foam generated during stirring of the emulsion,
   wherein $H_{fb}/H_{liquid}$ satisfies 0.2 to 0.5,
   where $H_{fb}$ is a depth from the surface of the emulsion to a center of the foam breaker, and
   $H_{liquid}$ is a depth from the surface of the emulsion to a bottom surface of the container.

2. The apparatus with the emulsion of claim 1, further comprising:
   a rotation shaft connected to the impeller to provide rotational force to the impeller,
   wherein the foam breaker is connected to the rotation shaft, and the impeller and the foam breaker rotate simultaneously by the rotation of the rotation shaft.

3. The apparatus with the emulsion of claim 1, wherein $D_{fb}/D_{main}$ satisfies 0.3 to 1,
   where $D_{main}$ is a diameter of the impeller, and
   $D_{fb}$ is a diameter of the foam breaker.

4. The apparatus with the emulsion of claim 1, wherein an inside of the container has a cylindrical shape; and
   $D_{fb}/D_{tank}$ satisfies 0.3 to 0.6,
   where $D_{tank}$ is a diameter of the container, and
   $D_{fb}$ is a diameter of the foam breaker.

5. The apparatus with the emulsion of claim 1, further comprising:
   a compressed air supply unit configured to supply compressed air to the surface of the emulsion in the container and an air discharge unit for discharging air in the container to an outside of the container.

6. The apparatus with the emulsion of claim 1, wherein $H_{fb}/D_{fb}$ is between 0.5 and 2,
   where $H_{fb}$ is the depth from the surface of the emulsion to the center of the foam breaker, and
   $D_{fb}$ is a diameter of the foam breaker.

7. The apparatus with the emulsion of claim 1, wherein the container comprises at least one baffle formed on an inner wall of the container, protruding toward a center of the container.

8. The apparatus with the emulsion of claim 7, wherein $H_{baffle}/H_{liquid}$ satisfies 0.6 to 0.8,
   where $H_{baffle}$ is a height from a bottom of the baffle to the surface of the emulsion, and
   $H_{liquid}$ is the depth from the surface of the emulsion to the bottom surface of the container.

9. The apparatus with the emulsion of claim 7, wherein an inside of the container has a cylindrical shape; and
   $W_{baffle}/D_{tank}$ satisfies 0.06 to 0.10,
   where $W_{baffle}$ is a height of the baffle protruding from the inner wall of the container, and
   $D_{tank}$ is a diameter of the container.

10. The apparatus with the emulsion of claim 1, further comprising:
    a compressed air supply unit configured to provide compressed air to a space above the emulsion in the container; and
    an air discharge pump for discharging air in the space to an outside of the container.

* * * * *